(12) United States Patent
Yeow (10) Patent No.: US 11,040,134 B2
(45) Date of Patent: Jun. 22, 2021

(54) MEDICAL TOOLS AND INTRAVENOUS SYSTEM

(71) Applicant: Linda Yeow, Yonkers, NY (US)

(72) Inventor: Linda Yeow, Yonkers, NY (US)

(*) Notice: Subject to any disclaimer, the term of this patent is extended or adjusted under 35 U.S.C. 154(b) by 209 days.

(21) Appl. No.: 16/387,214

(22) Filed: Apr. 17, 2019

(65) Prior Publication Data

US 2020/0330677 A1 Oct. 22, 2020

(51) Int. Cl.
*A61M 5/14* (2006.01)
*A61M 25/00* (2006.01)
*A61M 39/10* (2006.01)
*A61M 39/28* (2006.01)
*A61M 25/06* (2006.01)

(52) U.S. Cl.
CPC ........ *A61M 5/1413* (2013.01); *A61M 5/1407* (2013.01); *A61M 25/0026* (2013.01); *A61M 25/0606* (2013.01); *A61M 39/105* (2013.01); *A61M 39/1011* (2013.01); *A61M 2005/1403* (2013.01)

(58) Field of Classification Search
CPC ................ A61M 5/1407; A61M 39/10; A61M 2039/1077; A61M 5/1408; A61M 5/2448; A61M 5/1413; A61M 39/105; A61C 5/62; A61C 5/61
See application file for complete search history.

(56) References Cited

U.S. PATENT DOCUMENTS

| | | | | | |
|---|---|---|---|---|---|
| 3,316,935 | A | * | 5/1967 | Kaiser | A61M 39/287 137/595 |
| 4,257,416 | A | * | 3/1981 | Prager | A61M 5/1408 604/250 |
| 5,411,490 | A | * | 5/1995 | Tennican | A61M 5/1408 600/575 |
| 2003/0120217 | A1 | * | 6/2003 | Abergel | A61M 5/19 604/191 |
| 2003/0181874 | A1 | * | 9/2003 | Bressler | A61M 25/0631 604/263 |
| 2011/0301541 | A1 | * | 12/2011 | White | A61M 25/0637 604/164.04 |
| 2017/0239422 | A1 | * | 8/2017 | Kodgule | A61P 33/06 |
| 2019/0161229 | A1 | * | 5/2019 | Mase | G09F 3/00 |

OTHER PUBLICATIONS

MILA International, Inc.; 2016 Catalog; pp. 1-3, 16, 52 and last page; http://www.milainternational.com/media/wysiwyg/2016_US_Catalog_1.pdf, accessed Jan. 8, 2021. (Year: 2016).*
MILA International, Inc.; Extensions with MicroClave; https://www.milainternational.com/products/microclave/extensions-with-microclaver.html; accessed Jan. 8, 2021. (Year: 2021).*
Jorgensen Laboratories, Inc.; Large Bore IV Administration Set w/Coiled Tubing (J0400LN) & Dual Spike Extension Set (J0400E2); youtube.com video; https://www.youtube.com/watch?v=cyhJfOuFckA; accessed Jan. 8, 2021; published Aug. 1, 2018. (Year: 2018).*

* cited by examiner

*Primary Examiner* — Daniel J Colilla (57) ABSTRACT

An introduction of medical tools to this invention that enables the improvement of flushing of sterile solutions, medications and the collection of blood specimen(s). In addition, an introduction of intravenous system whereby the healthcare provider can perform the tasks of flushing the intravenous site efficiently and collecting blood specimen using the combination of medical tools. Most importantly, these tools included in this invention preserve and protect intravenous lines from malfunctioning.

3 Claims, 9 Drawing Sheets

IV Catheter Line System®

Heparin n' Line V-Syringe®

Fig. 4

Y-Combo Connector®

MEDICAL TOOLS AND INTRAVENOUS SYSTEM

BACKGROUND OF INVENTION

The purpose of this invention is to maintain patency for patients with intravenous catheter lines and to preserve the intravenous catheter lines with proper care. Patients with intravenous lines require proper flushing in the catheter lines for maintenance before and after receiving medications or collecting blood specimen(s) through the medical lines. If proper flushing through the intravenous lines are facilitated with this invention, intravenous lines can be preserved with proper care. The introduction of utility tools used in this invention are important to the healthcare system because it provides a solution to intravenous lines from malfunctioning and to better improve the flushing of the intravenous lines at site efficiently.

SUMMARY

By introducing these utility tools into the healthcare system, I am introducing this invention which can reduce intravenous line malfunctioning. The disclosure of these tools can help to alleviate problems for patients with intravenous lines. Patients with intravenous lines can preserve their lines with proper care received by a healthcare provider. And hence, this invention will allow a better improvement to provide proper care for patients with intravenous lines. In the present application, the innovation will become supportive and discussed in the detailed description.

BRIEF DESCRIPTION OF THE DRAWINGS

In the presentation of this entire invention, you will see drawings of the utility tools introduced. I will share about each drawing does and their uses. In order for the invention to work, some of the tools work interdependently on one another to make the task work.

In FIG. 1, it shows a clamp labeled (FIG. 1a) attached to a flex catheter line with an infusion port at the end. In FIG. 1, it shows a clamp labeled (FIG. 1b) attached to a flex catheter line with an infusion port at the end. In the drawing FIG. 1, it shows a clamp labeled (FIG. 1c) proximal to the needle of the catheter line system. The clamps on the IV Catheter Line System® serves to prevent administration of medication(s) into the line when clamped.

In FIG. 2 drawing, it shows a drawing of a joint double syringes. I named it as Saline n' Line V-Syringe®. It is a medical tool that is used for administering medication and flushing of sterile solution before and after administering medication. It comprises of a double syringe where the left-side syringe labeled (FIG. 2a) contains prefilled normal saline 0.9% Sodium Chloride Sterile Solution Rx only, and the right-side syringe labeled (FIG. 2b) is an empty-filled syringe. The right-side syringe labeled (FIG. 2b) can be filled up with medication. In the drawing of FIG. 2, there is a safety lock needle labeled (FIG. 2c) and it is used to draw up medication into the right-side syringe (FIG. 2b).

In FIG. 4 drawing, it shows a drawing of a joint double syringes. I named it as Heparin n' Line V-Syringe®. This medical tool is designed to prepare administering heparin in medical lines. In this drawing, the left-side syringe labeled (FIG. 4a) contains prefilled heparin lock flush Rx only and on the right-side of the syringe, it is an empty-filled syringe labeled (FIG. 4b). In FIG. 4, medication can be drawn into the right-side of syringe (FIG. 4b) using a safety lock needle (FIG. 4c).

In FIG. 5 drawing, it shows a drawing of a two-way split infusion port connector. I named it as Y-Combo Connector® and it is a medical tool. The Y-Combo Connector® comprises of a two-way split infusion port with three clamps on it. In the drawing of FIG. 5, there is a clamp on the flex catheter line attached to a left-side infusion port line labeled (FIG. 5a), a clamp on the right-side infusion port line labeled (FIG. 5b) and a clamp labeled (FIG. 5c) attached close to the end of the blunt male connector. This medical tool serves as an important connection as it can attach itself onto a peripherally inserted central catheter (PICC) port access to prepare administering medication purposes. The connector is a two-way flushed system that enables the flushing of sterile solution and administering medication on each infusion port end. The clamps on the Y-Combo Connector® serves as a gate-keeper to prevent administration of medication(s) through the line.

In FIG. 8 drawing, it shows a blood collection kit. I named it as the Blood Collection Kit®. This medical tool enables you to collect blood specimen(s). The drawing shows a joint double syringes which are emptied filled, and enclosed with white caps at the end of the syringes. The left-side syringe labeled (FIG. 8a) is called a second blood draw syringe and the right-side syringe labeled (FIG. 8b) is called the first blood draw syringe. Below the drawing of FIG. 8, there is a sharp vacutainer labeled (FIG. 8c), which serves as a purpose to attach itself to syringe (FIG. 8a) for use of transferring blood into a blood specimen tube.

DETAILED DESCRIPTION

In the following detailed description of the invention, it should keep in mind that there are several medical tools introduced that can be used interdependently to make a task possible. In the presentation of my tools, I will indicate the use of each tool and how each tool plays a role to make the task possible. The tools introduced are interdependent and it relies upon one another to perform a task.

Figure 1:
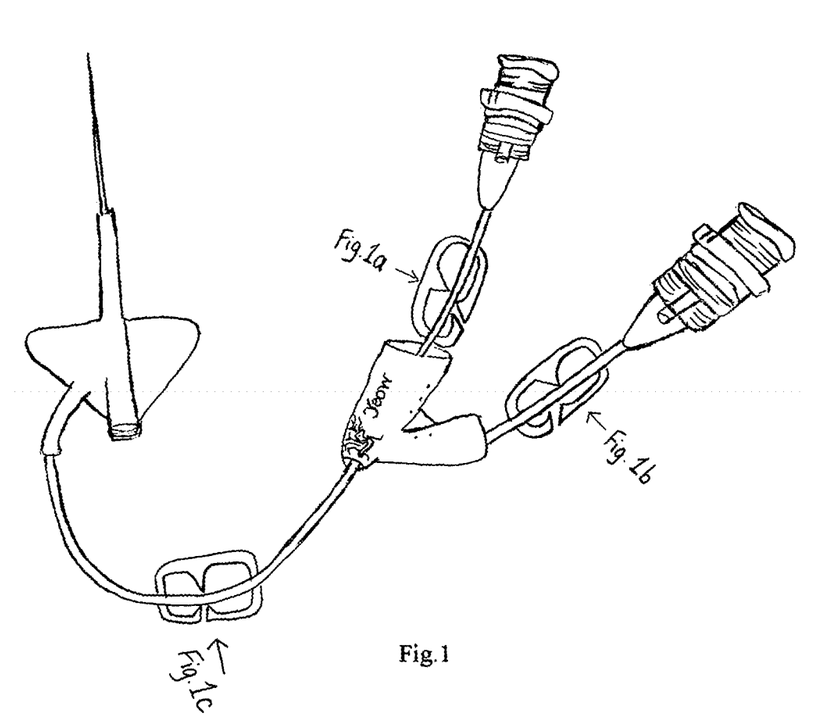
In FIG. 1 drawing, it shows a drawing of a catheter line system. I named it as IV Catheter Line System®. It is an intravenous catheter line system that can be inserted into a patient's peripheral extremity for administering medication(s).
Figures 2, 2A, 2B, 2C:
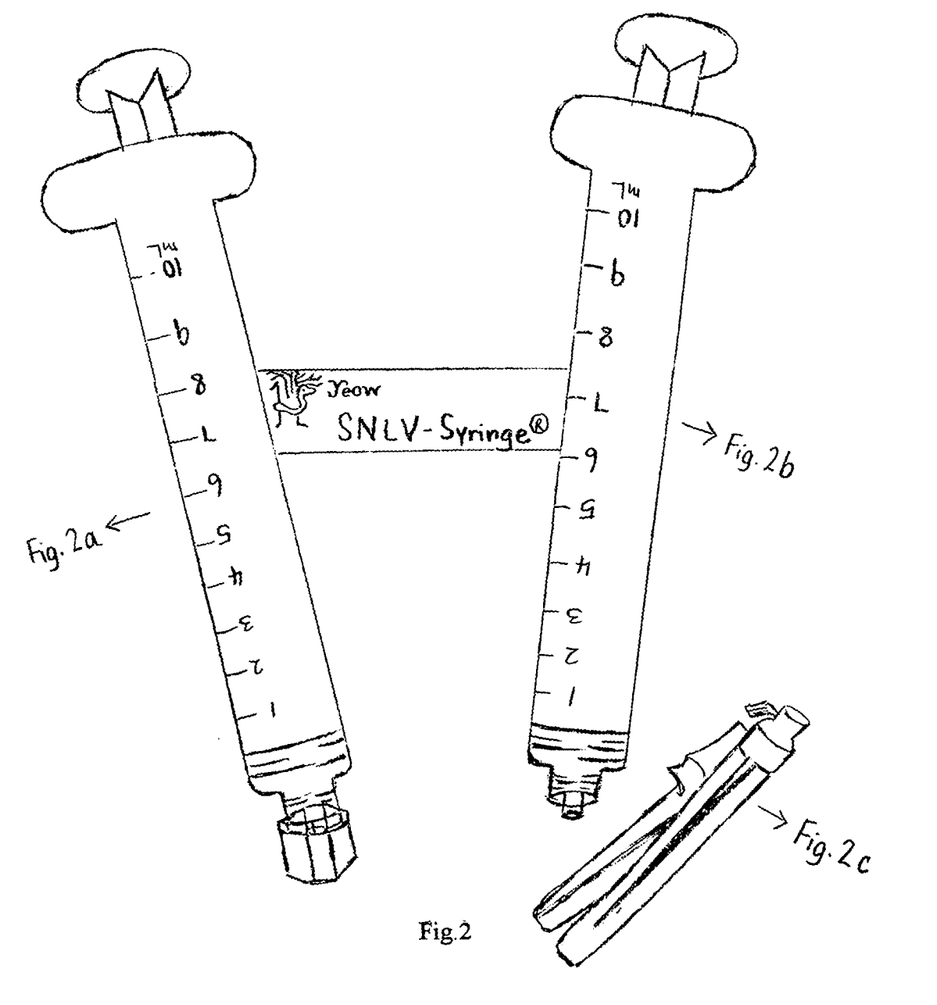
Figure 3:
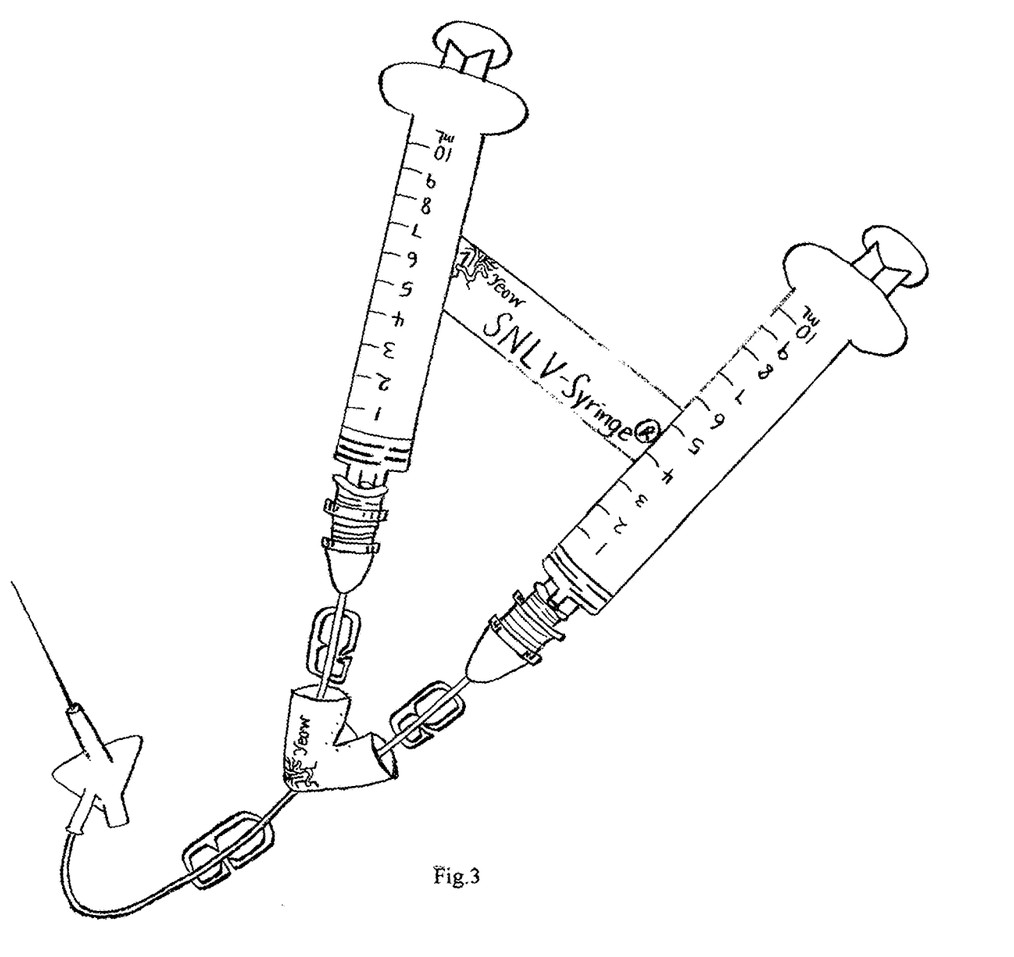
In FIG. 3 drawing, it shows a combination of drawing FIG. 1 and FIG. 2 when they are attached and used interdependently together. This drawing shows how you will attach the joint double syringes, Saline n' Line V-Syringe® to the IV Catheter Line System® when in use.

In the invention of Saline n' Line V-Syringe®, it uses the IV Catheter Line System® to perform flushing and administering medication efficiently. Looking at the IV Catheter Line System® in FIG. 1, clamp all the locks first. Draw medication into the syringe labeled (FIG. 2b) by using a safety lock needle labeled (FIG. 2c). After drawing the medication into the syringe (FIG. 2b), you will detach the needle by enabling the safety lock on the needle, and disposing the needle into the waste container of the facility. Next, you can attach the Saline n' Line V-Syringe® onto the IV Catheter Line System® for administering the medication. When attaching the Saline n' Line V-Syringe® onto the IV Catheter Line System®, match the parts of the syringe labeled (FIG. 2a and FIG. 2b) to the infusion ports of the IV Catheter Line System® labeled (FIG. 1a and FIG. 1b) respectively and attach them securely together. After attaching it securely, open the clamps of (FIG. 1a and FIG. 1c). Next, you can flush about 5 ml of the prefilled normal saline sterile solution from the syringe (FIG. 2a). After flushing the saline solution, clamp the lock on (FIG. 1a) and open the clamp on (FIG. 1b) to prepare the administering the medication from syringe (FIG. 2b). After administering the medication, clamp the lock on the (FIG. 1b). Next, open the clamp on (FIG. 1a) and flush the remaining saline solution from the syringe (FIG. 2a). After flushing the line with saline solution, clamp the locks of (FIG. 1a and FIG. 1c) on the IV Catheter Line System®. Finally, detach the Saline n' Line V-Syringe® from the IV Catheter Line System® and discard it. In FIG. 3 drawing, you can find the drawing of the Saline n' Line V-Syringe® and the IV Catheter Line System® attached together when in use.

Figures 4, 4A, 4B, 4C:
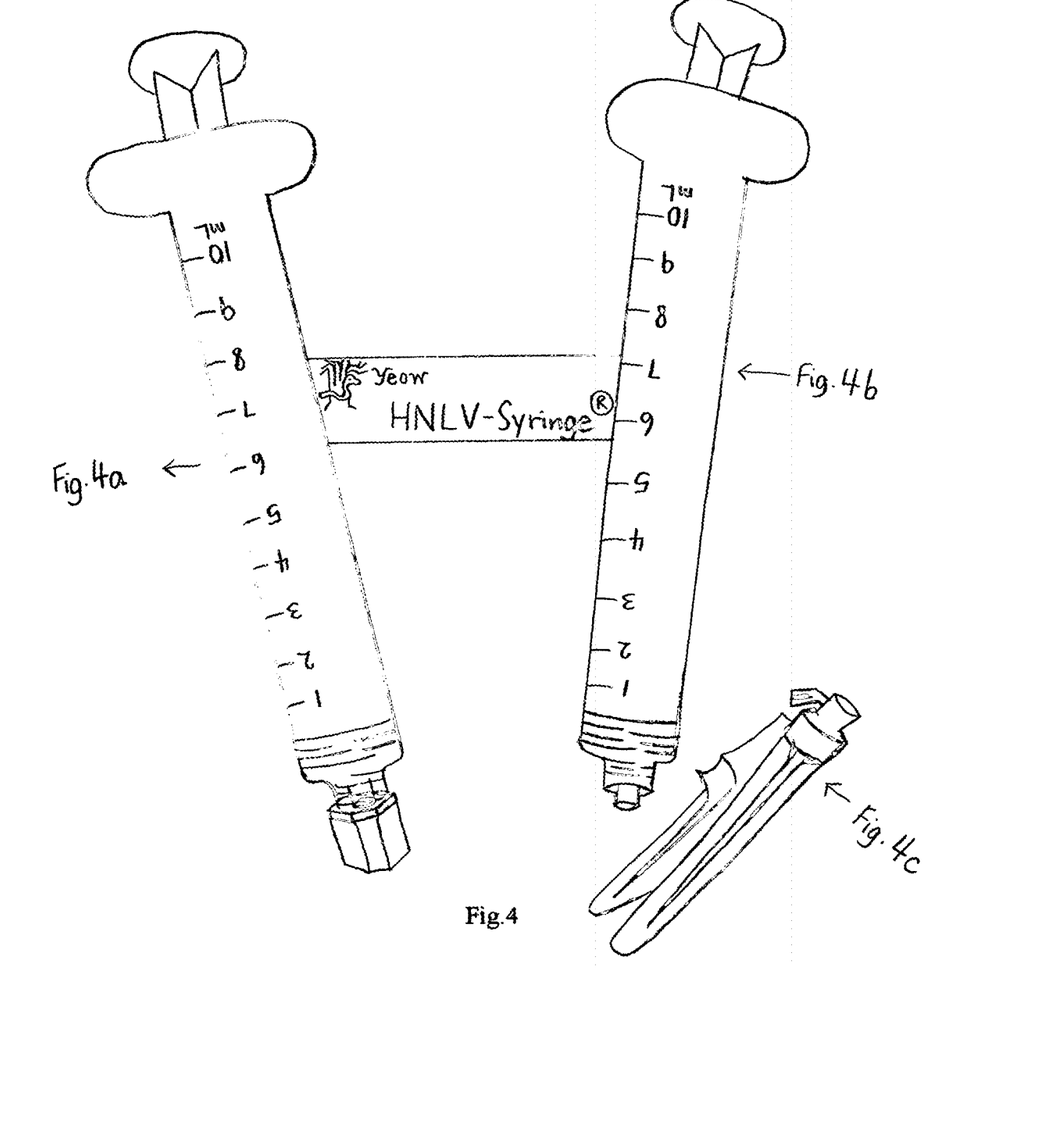
Figure 5:
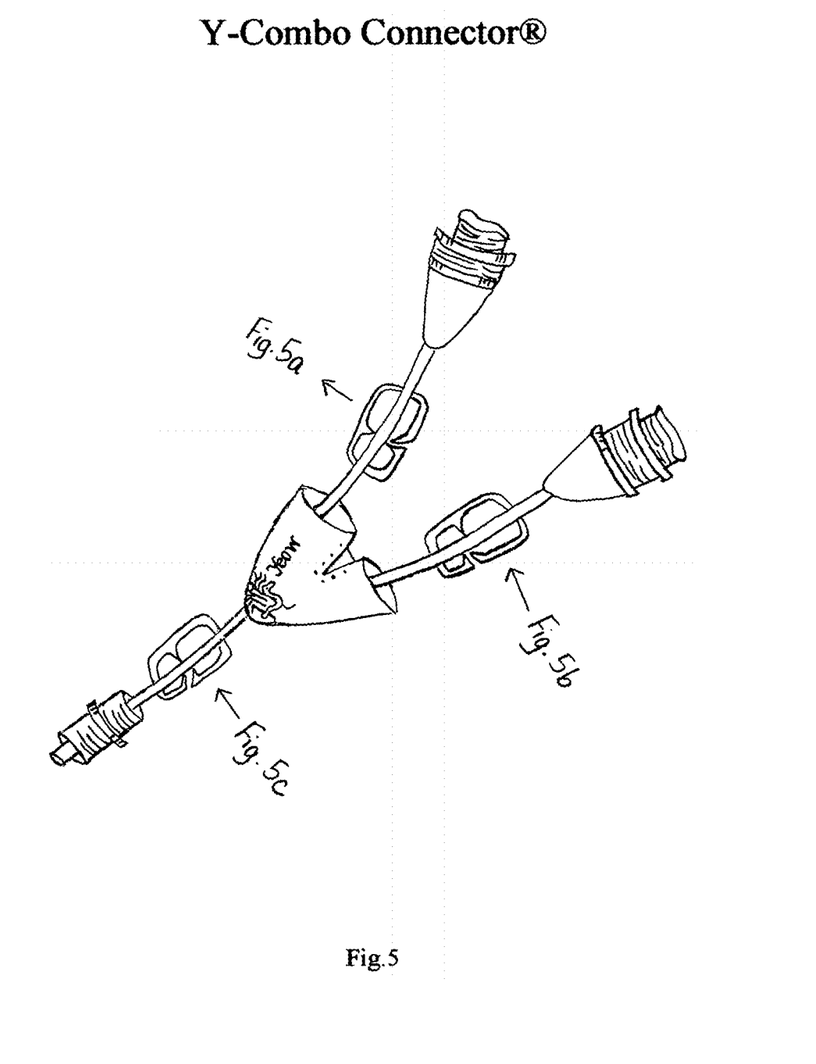
Figure 6:
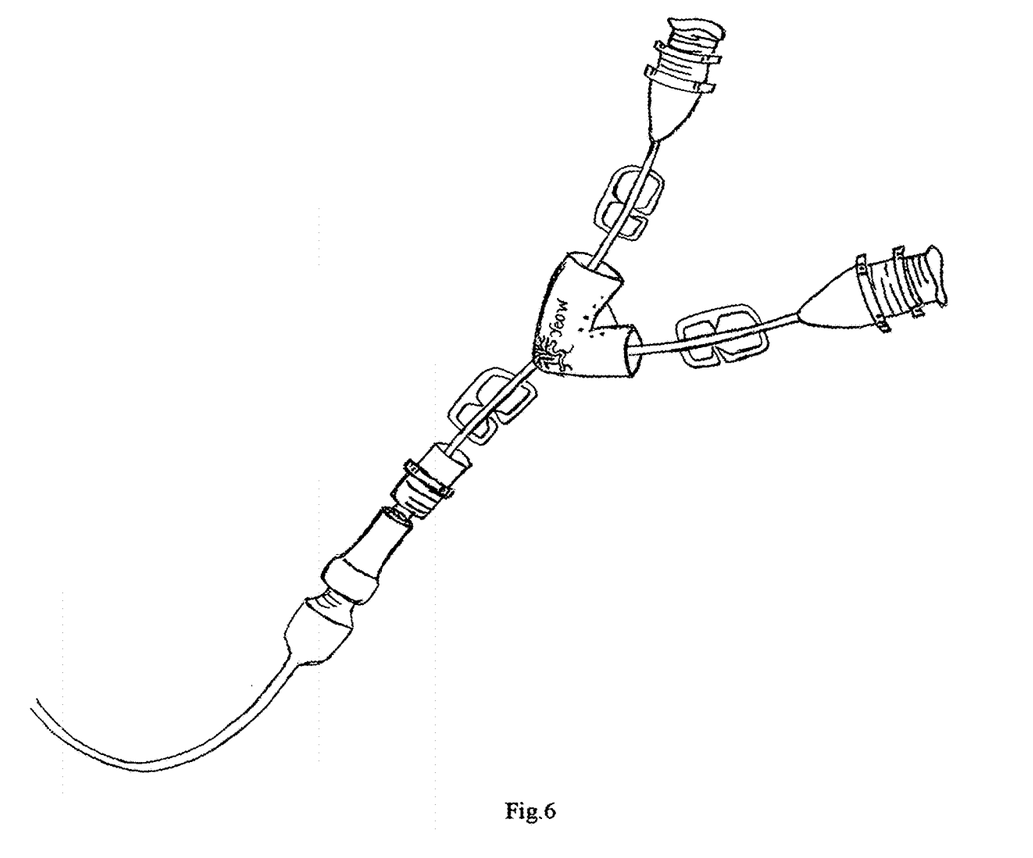
In FIG. 6 drawing, it shows how a Y-Combo Connector® can be attached to a single lumen PICC access for medical uses. By attaching the Y-Combo Connector onto the PICC port, it will enable the healthcare provider to flush the PICC line with medication and heparin efficiently.
Figure 7:
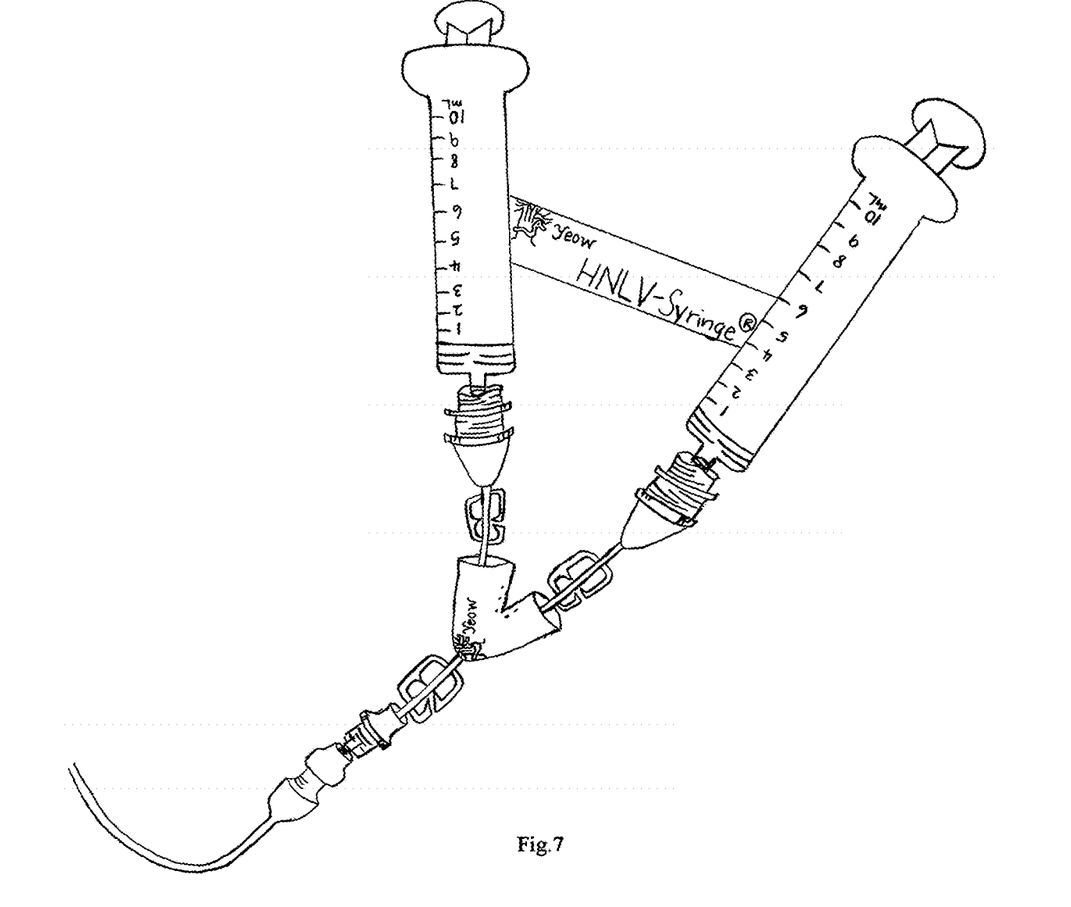
In FIG. 7 drawing, it shows how you can administer heparin through a PICC port using the Heparin n' Line V-Syringe® and the Y-Combo Connector®. The drawing shows an image of where the Heparin n' Line V-Syringe® would be attach onto the Y-Combo Connector®, and then displaying how medication and heparin can be administered through the single lumen PICC line.

In the invention of Heparin n' Line V-Syringe®, it utilizes the aid of a Y-Combo Connector® to flush heparin medication into medical lines and PICC line. First, attach the Y-Combo Connector® into a medical line or PICC line port. Next, you can draw normal saline sterile solution into the syringe labeled (FIG. 4b) by using a safety lock needle labeled (FIG. 4c). After drawing the normal saline sterile solution into the syringe (FIG. 4b), detach the needle by enabling the safety lock on the needle and disposing the needle into the facility sharp waste container. Then, affix the Heparin n' Line V-Syringe® to the Y-Combo Connector®, making sure all clamps are closed. When attaching the Heparin n' Line V-Syringe® to the Y-Combo Connector®, match the parts of the syringe labeled (FIG. 4a and FIG. 4b) to the Y-Combo Connector® infusion port lines labeled (FIG. 5a and FIG. 5b) respectively and attach them securely together. After attaching the Heparin n' Line V-Syringe® onto the Y-Combo Connector®, open the clamps of (FIG. 5b and FIG. 5c) and check to open the clamp on the PICC line if any. Next, begin flushing the normal saline solution through the PICC line from the syringe labeled (FIG. 4b). After flushing the PICC line with normal saline solution, close the clamp of (FIG. 5b) and open the clamp of (FIG. 5a) for preparation to administer the prefilled heparin lock flush medication. When administering heparin, it must be used cautiously and prescribed by the healthcare provider. After administering the prefilled heparin medication, clamp the locks on (FIG. 5a and FIG. 5c) and check to close the clamp on the PICC line if any. Finally, detach the Y-Combo Connector® from the PICC line port and discard it. In FIG. 6 drawing, it shows how the Y-Combo Connector® affix itself on the single port PICC line for preparation of heparin administration. In FIG. 7 drawing, you can see a full drawing of how the Heparin n' Line V-Syringe® and the Y-Combo Connector® work interdependently to administer medication and heparin through the PICC line.

Figures 8A, 8C:
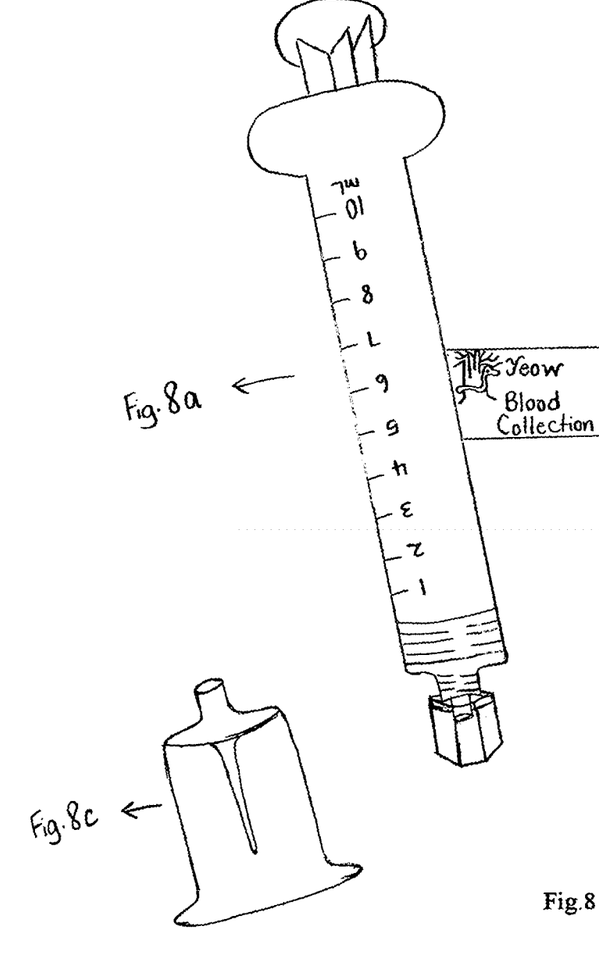
Figure 8B:
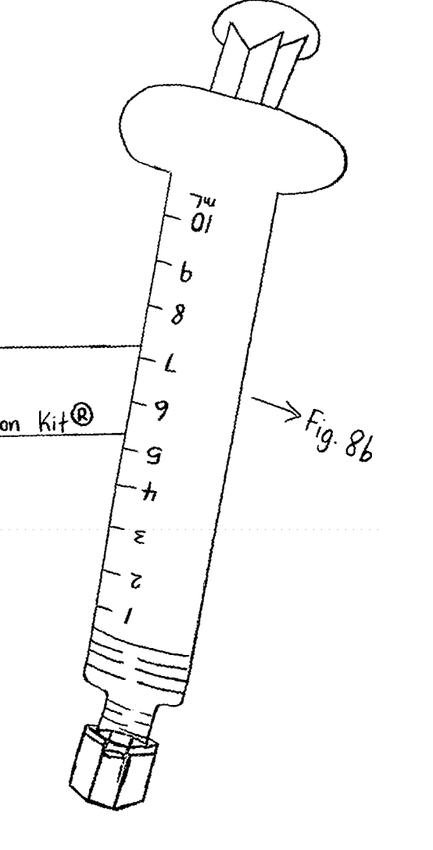

The Blood Collection Kit® shown in FIG. 8 is used to collect blood specimen from a single lumen PICC line. To begin, remove the secured white caps of the joint double syringes in the kit. First, attach the Y-Combo Connector® to the PICC port access, making sure all the clamps on the Y-Combo Connector® are closed. Next, attach the Blood Collection Kit® to the Y-Combo Connector®, matching the parts of the joint double syringes labeled (FIG. 8a and FIG. 8b) to the Y-Combo Connector® infusion ports labeled (FIG. 5a and FIG. 5b) respectively and attach them securely together. After attaching the Blood Collection Kit® to the Y-Combo Connector®, open the clamps of (FIG. 5b and FIG. 5c) and keeping the clamp labeled (FIG. 5a) close on the Y-Combo Connector®. Then, check for any clamp from the medical line or PICC line. If any clamp is found on the PICC line, open the clamp to prepare withdrawing blood specimen. Next, withdraw the first 10 ml of blood into syringe labeled (FIG. 8b) with the plunger in the syringe. After successfully withdrawing the first 10 ml of blood, close the clamp of (FIG. 5b) and open the clamp of (FIG. 5a) on the Y-Combo Connector®. Now, withdraw another 10 ml of blood into the syringe of (FIG. 8a) by pulling on the plunger in the syringe slowly. After collecting the second withdrawal of blood specimen into the syringe of (FIG. 8a), close the clamps of (FIG. 5a and FIG. 5c) on the Y-Combo Connector®. The next step requires careful disconnection of the Blood Collection Kit®. When detaching the Blood Collection Kit® from the Y-Combo Connector®, slowly unfastened the syringes of the Blood Collection Kit® and replace the end of the syringe labeled (FIG. 8b) with a white cap. Next, attach a sharp vacutainer labeled (FIG. 8c) to the syringe of the Blood Collection Kit® labeled (FIG. 8a).

Figure 9:
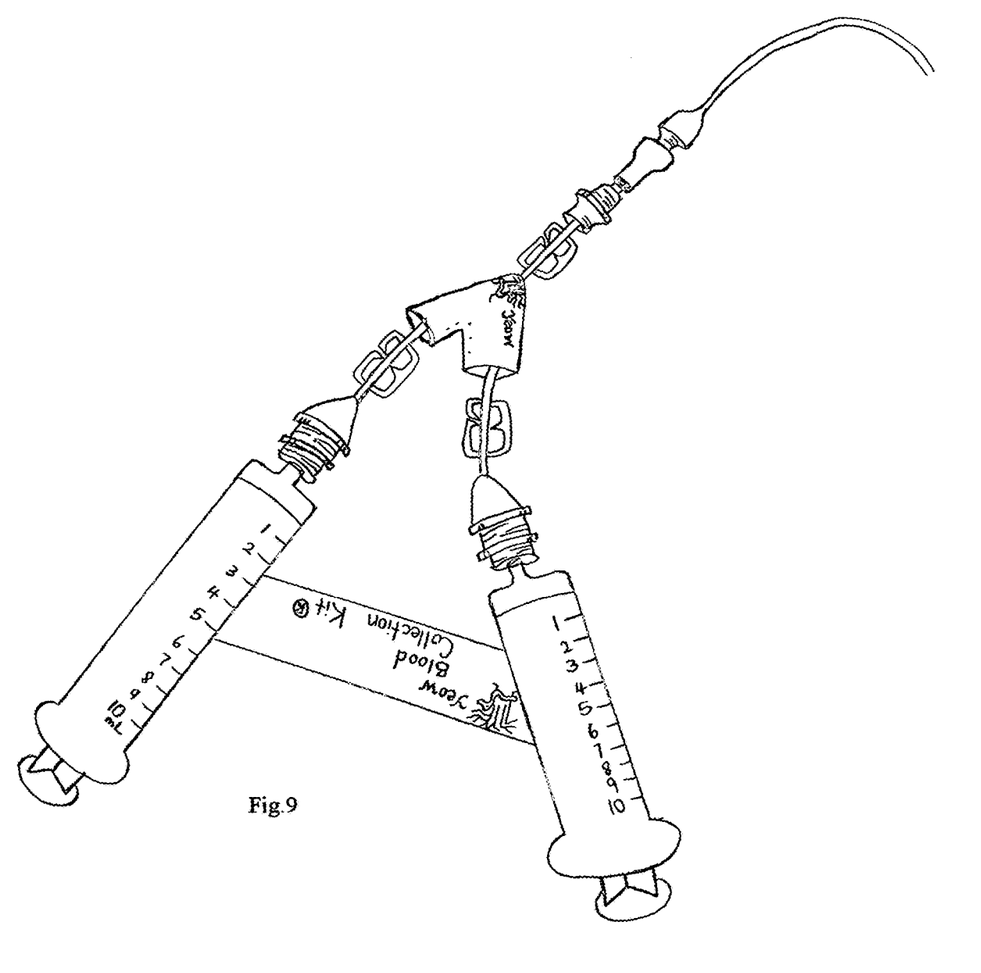
In FIG. 9 drawing, it shows a drawing of how the Blood Collection Kit® attached to the Y-Combo Connector®, and enables the collection of blood specimen from a single lumen PICC port access line. The Blood Collection Kit® can affix itself to the Y-Combo Connector®, while the Y-Combo Connector® can be attached to the single lumen PICC port access for blood collection.

Finally, insert a blood specimen tube at the end of the vacutainer and blood will be collected from the syringe (FIG. 8a). After blood collection, discard the Blood Collection Kit® into the waste container located in the facility. Next, flush the PICC line with appropriate care and cap the line after. In FIG. 9 drawing, it shows how the Y-Combo Connector® and the Blood Collection Kit® are connected together to a single lumen PICC port access. Thus, the drawing shows the collection of blood specimen is carried out when combining the use of the Blood Collection Kit® and the Y-Combo Connector® attached to a single lumen PICC line.

The invention claimed is:

1. An intravenous catheter line system with a size needle at one end comprising:
    a double syringe medical tool including a first syringe and a second syringe connected by a firm bridge which includes a planar portion configured to receive a brand logo, wherein the firm bridge connects a cylindrical side of the first syringe to a cylindrical side of the second syringe;
    a two-way split infusion port,
    wherein each syringe is connected to a respective input end of the two-way split infusion port with a first and second flex catheter line, respectively and the size needle is connected to an output end of the two-way split infusion port with a third flex catheter line;
    a first clamp disposed on the first flex catheter line;
    a second clamp disposed on the second flex catheter line; and
    a third clamp disposed on the third flex catheter line;

wherein the first syringe may include normal saline solution while the second syringe may include an empty syringe;

and wherein the first syringe is configured to attach to a cap and the second syringe is configured to attach to a safety lock needle.

2. A two-way split infusion port connector comprising:

a first infusion port;

a second infusion port;

an outlet port;

a double syringe medical tool including a first syringe and a second syringe connected by a firm bridge which includes a planar portion configured to receive a brand logo, wherein the firm bridge connects a cylindrical side of the first syringe to a cylindrical side of the second syringe, wherein the first syringe is connected to the first infusion port by a first flex catheter line, the second syringe is connected to the second infusion port by a second flex catheter line, and the outlet port is connected to a third flex catheter line;

a first clamp disposed on the first flex catheter line;

a second clamp disposed on the second flex catheter line; and a third clamp disposed on the third flex catheter line;

a blunt male connector with the two-way split infusion port connector, wherein the first syringe may include heparin lock flush solution and the second syringe may include an empty syringe, and wherein the first syringe is configured to attach to a cap and the second syringe is configured to attach to a safety lock needle.

3. A blood collection kit comprising:

a double syringe medical tool including a first empty syringe and a second empty syringe connected by a firm bridge which includes a planar portion configured to receive a brand logo, wherein the firm bridge connects a cylindrical side of the first syringe to a cylindrical side of the second syringe;

a two-way split infusion port secured with the intravenous catheter line system;

wherein each syringe is connected to a respective input end of the two-way split infusion port with a first and second flex catheter line, respectively and the size needle is connected to an output end of the two-way split infusion port with a third flex catheter line;

a first clamp disposed on the first flex catheter line;

a second clamp disposed on the second flex catheter line; and a third clamp disposed on the third flex catheter line, wherein the first syringe is configured to attach to a cap and the second syringe is configured to attach to a sharp receptacle that has a partial vacuum to facilitate the collection of a blood specimen.

\* \* \* \* \*